United States Patent

Quintanilla Almagro et al.

(10) Patent No.: US 6,699,512 B2
(45) Date of Patent: Mar. 2, 2004

(54) ***HYPERICUM PERFORATUM* L. OLEORESIN, PROCEDURE FOR OBTAINING IT AND USES OF IT**

(75) Inventors: Eliseo Quintanilla Almagro, Alicante (ES); Ana Ramirez Bosca, Alicante (ES); August Abernd, Alicante (ES); José Pardo Zapata, Alicante (ES); Joaquín Diaz Alperi, Alicante (ES); David Pamies Mira, Alicante (ES); Miquel Angel Carrion Gutierrez, Alicante (ES)

(73) Assignee: Asac, Compañia de Biotechnologia e Investigacion, S.A., Alicante (ES)

( * ) Notice: Subject to any disclaimer, the term of this patent is extended or adjusted under 35 U.S.C. 154(b) by 2 days.

(21) Appl. No.: 09/959,647

(22) PCT Filed: Mar. 2, 2001

(86) PCT No.: PCT/ES01/00080

§ 371 (c)(1),
(2), (4) Date: Apr. 22, 2002

(87) PCT Pub. No.: WO01/66121

PCT Pub. Date: Sep. 13, 2001

(65) Prior Publication Data

US 2002/0197337 A1 Dec. 26, 2002

(30) Foreign Application Priority Data

Mar. 6, 2000 (ES) .......................... 200000586

(51) Int. Cl.$^7$ ................................................ A61K 35/78
(52) U.S. Cl. ....................................... 424/730; 424/725
(58) Field of Search ................................ 424/730, 725

(56) References Cited

U.S. PATENT DOCUMENTS 6,224,906 B1 * 5/2001 Ghosal
6,238,671 B1 * 5/2001 Joseph
6,280,736 B1 * 8/2001 Erdelmeier et al.
6,291,241 B1 * 9/2001 Castor et al.

FOREIGN PATENT DOCUMENTS

WO    WO 9964027    12/1999

OTHER PUBLICATIONS

Maisenbacher et al, *Planta Med.*, 58(4):351–354 (1992).
Hölzl et al, *Planta Med.*, 55(7):601–602 (1989).
Orth et al, *Drugs Made In Germany*, 42(4):110–113 (1999).

* cited by examiner

Primary Examiner—Christopher R. Tate
(74) Attorney, Agent, or Firm—Sughrue Mion, PLLC

(57) ABSTRACT

*Hypericum perforatum* L. Oleoresin, procedure for obtaining it and uses of it. A *Hypericum perforatum* L Oleoresin is describes that is stable over time on its Hyperforin and Hypericine content without adding preservatives; a procedure for obtaining the Oleoresin by extraction with low-polarity solvents, followed by purification; also its use as a regulator of the components of the extracellular matrix is described and its use for the manufacture of hydrosoluble gels containing *Hypericum perforatum* L Oleoresin.

17 Claims, No Drawings

HYPERICUM PERFORATUM L. OLEORESIN, PROCEDURE FOR OBTAINING IT AND USES OF IT

This application is a §371 of PCT/ESO1/00080, filed Mar. 2, 2001, which is incorporated in its entirety herein by reference.

TECHNICAL FIELD OF THE INVENTION

The present invention describes an oleoresin or lipidic extract of *Hypericum perforatum* L., which contains hypericine and is enriched with hyperforins, and is stable over time without adding stabilisers. The extract is obtained by extraction with low-polarity solvents and then purification by re-extraction with alcanols-water. The invention describes the use of the oleoresin to regulate the components of the extracellular matrix in a dose dependent manner.

The invention also relates to hydrosoluble gels, the active ingredient of which is *Hypericum perforatum* L., to be used as cicatrizants.

BACKGROUND OF THE INVENTION

*Hypericum perforatum* L has long been used by popular medicine, as a cicatrizant and in the treatment of burns.

The chemical species present in *Hypericum perforatum* L include acilfloroglucinols: hyperforins and adhyperforins; *Hypericum perforatum* also contains naptodiantrones: hypericine and pseudohypericine. These compounds are responsible for the activity of the extracts in the treatment of wounds and scars, but these products are unstable when attempting to obtain them in pure form, and over time they decompose due to the effect of light and heat.

European patent EP0854726 describes obtaining stable *Hypericum perforatum* L extracts by adding antioxidant preservatives such as ascorbic acid, cysteine and/or glutathione, extracting the plant with organic solvents or alcohol-water mixes.

On the other hand, the pharmaceutical formulations described in state of the art DE2406452 are ointments containing an active ingredient consisting of fresh Hypericum leaves and oily excipients (olive oil, bees wax, fatty acid esters, etc.), providing a lipophylic ointment that is insoluble in water.

However, these oily formulations lead to a maceration of the skin after prolonged use, and have a reduced bioavailability making it difficult to wash the lesions, and therefore to monitor their condition.

As mentioned earlier, *Hypericum perforatum* L extracts have shown different pharmacological activities, mainly as cicatrizants, but to date their effect on the modulation of the extracellular matrix (ECM) of the fibroblasts. The collagen components are therefore responsible for the mechanical properties of the skin, whereas tenascine is responsible for the regulation of the adhesion molecules and migration in cicatrisation processes.

The technical problem of the invention is providing stabilised extracts of *Hypericum perforatum* L., without adding stable preservatives, without losing its active ingredients and preserving its pharmacological properties. Moreover, its use in a hydrosoluble and stable pharmaceutical composition containing *Hypericum perforatum* L extract enriched in hyperforins to avoid the maceration of the skin that takes place with treatment with lipophylic ointments and creams, improving bioavailability and the evaluation of the lesions.

SUBJECT OF THE INVENTION

Surprisingly, the invention is bases on the stability of the lipidic extracts of *Hypericum perforatum* L., which contain all its natural components: hyperforins and hypercins, in a lipidic matrix, and are stable over time without adding preservatives. The lipidic extracts or oleoresins are obtained with low-polarity solvents capable of extracting the lipidic components of the drug, followed by purification by re-extraction with alcanols-water.

The extracts have more than 10% content in hyperforins and more than 0.5% in hypericines, in a lipidic matrix that stabilises the active ingredients of *Hypericum perforatum* L.

The extracts have shown a dose-dependent activity in the regulation of the production of the components of the extracellular matrix, thus avoiding the possible toxicity of the product by inhibiting the production of collagen and tenascine at high doses and, on the other hand, avoiding the formation of hypertrophic and cheloid scars.

The aforementioned extracts can be used in pharmaceutical preparations such as hydrosoluble gels as cicatrizant agents that improve bioavailability, prevent the maceration of the skin, and improve the application of the product compared with the formulations described by the state of the art based on oily or lipophylic excipients. Moreover, with hydrosoluble gels it is possible to better monitor the lesions, since they are transparent.

DETAILED DESCRIPTION OF THE INVENTION

The invention is based on the stability of *Hypericum perforatum* L extracts, characterised by the presence of hypericine and hyperforins in a lipidic matrix.

The extracts are obtained first by the extraction of *Hypericum perforatum* L with a low-polarity solvent, followed by re-extraction with hot alcohol-water mixes, obtaining a fluid oleoresin with over 10% content in hyperforins and more than 0.5% content in hypericines.

The fluid *Hypericum perforatum* L oleoresins obtained by extraction with low-polarity solvents, followed by hot mixes of alcanols with low molecular weight and water, have been seen to be stable, without losing their hyperforin content due to the effect of light and temperature. The hyperforin content after one year of storage at 40° C., exposed to the light and room temperature, has shown a hyperforin content of 15%.

In a preferred embodiment of the invention to prepare the extract, the *Hypericum perforatum* L is extracted at a low temperature with solvents with a polarity below 0.6. The solvent to be used is not critical, and different mixes can be employed.

The plant is extracted in the proportion of one part drug to 6 parts solvent, by maceration for 24 hours at a temperature less than or equal to 20° C. It is then filtered and the drug is extracted again by maceration for 24 hours, and so on until extraction is complete.

The extracts in liquid form are concentrated to obtain a bland and fluid syrup, by high vacuum and a temperature below 40° C.

The bland fluid syrup is purified by dissolution in an alcanols-water mix and filtered, preferably using alcohols of low molecular weight, such as methanol, ethanol or isopropanol. The solution is prepared at 40–50° C., filtered and concentrated at reduced pressure, obtaining a fluid oleoresin.

With this extraction procedure, the oleoresins obtained have a high content in hyperforins of 10–15% and a content in hypericines of 0.5%, stable over time, determined by chromatographic or spectrophotometric techniques. In order to optimise the extraction procedure, additional steps can be added, such as selecting the initial raw materials with a hyperforin content of over 2%, dehydration of the raw materials at a temperature below 35° C., cryogenisation of the plant, etc.

On the other hand, according to the invention, hydrosoluble gels are obtained that facilitate the release of liposoluble *Hypericum perforatum* L oleoresin, permitting diffusion between the structures of the corneal layer, obtaining more bioavailability than the oily solutions. These hydrosoluble gels contain dilutant, humidifying, gelifying, emulsifying and preservative agents.

In one way of embodying the invention, the preservatives are dissolved in water and the *Hypericum perforatum* L oleoresin is dissolved in the emulsifiers. This mix is added to the preservatives dissolved in water, followed by the slow addition of the humidifying and gelifying agents, avoiding the occlusion of air.

Preferably water is used as a dilutant, glycerine as a humidifier, glyceril palmitate as a gelifier, parabenes as preservatives and PEG-40-hydrogenated Castor Oil, Polysorbate-20 and Octoxinole-11 as emulsifiers.

The preferred proportions for the invention are as follows:

| | |
|---|---|
| Hypericum oleoresin | 0.1–0.5% |
| Water | 60–80% |
| Glycerine and glyceril Polyacrilate | 20–30% |
| PEG-40-Hydrogenated castor oil, Polysorbate-20 y Octoxinole-11 | 1–3% |
| Parabenes | 0.2–0.4% |

Hypericum oleoresins regulate the production of the components of the extracellular matrix (ECM) such as collagen and tenastin, but surprisingly, this regulation is dose-dependent.

*Hypericum perforatum* L oleoresins at low concentrations (0.5–1 µg/ml) increase the production by 70% of the synthesis of collagens in fibroblast cultures, but at concentrations greater than 5 µg/ml, collagen synthesis is inhibited, avoiding the possible toxicity of the product and avoiding the formation of hypertrophic or cheloid scars.

According to the results obtained in the invention, the production of tenascine decreases after the treatment of the fibroblasts with Hypericum oleoresin for 24 h at 37° C. in a dose-dependent manner.

Following is a description of the invention using characteristic examples, to which the scope of the invention is not limited.

EXAMPLE 1
Illustrating the Procedure for Obtaining Oleoresins from *Hypericum perforatum* L 100 kilos of dehydrated *Hypericum perforatum* L flowers and leaves, at less than 35° C. and with a hyperforin content of greater than 2%, are macerated with 600 litres of methylene chloride: acetone (50:50) for 24 hours at 20° C. This process is repeated 3 more times until extraction is complete. The liquid extracts are concentrated in a vacuum and at a temperature below 40° C. to obtain 8 kilos of a bland fluid syrup. The previous extract is solubilised in a 100 litre mix of ethanol: water (60:40) at 50° C. by stirring for 2 hours and it is purified by filtering through a 5 micrometers membrane. The filtrate is of reduced concentration and obtains a hot fluid oleoresin that changes to paste form when cooled. This obtains 7.5 kilos of *Hypericum perforatum* L oleoresin with a hyperforin content of 14% and a hypericine content of 0.6%.

EXAMPLE 2
Illustrating the Stability of the Extracts.

1.—Stability at Room Temperature

| % | Hyperforin | Adhyperforin | Total Hyperforins |
|---|---|---|---|
| T = 0 | | | |
| Extract A | 7.7% | 7.3% | 15% |
| Extract B | 7.1% | 6.7% | 13.8% |
| Extract C | 7.7% | 7.2% | 14.9% |
| Extract D | 0.6% | 0.4% | 1% |
| T = 12 months at 25° C. | | | |
| Extract A | 7.4% | 7.2% | 14% |
| Extract B | 8.6% | 7.0% | 15.6% |
| Extract C | 7.2% | 7.5% | 14.9% |
| Extract D | 0.1% | 0.1% | 0.2% |

Where extracts A, B and C are *Hypericum perforatum* L oleoresins obtained according to the invention and extract D is a *Hypericum perforatum* L oleoresin obtained by extraction with ethanol, water (50:50).

The content in hyperforin was determined by HPLC.

2.—Stability at 40° C.

| Hyperforin | Adhyperforin | Total Hyperforins |
|---|---|---|
| T = 0 | | |
| 7.7% | 7.,3% | 15% |
| T = 12 months at 40° C. | | |
| 7.2% | 6.9% | 14.1% |

3.—Stability in the Presence of Light

| Hyperforin | Adhyperforin | Total Hyperforins |
|---|---|---|
| T = 0 | | |
| 7.7% | 7.3% | 15% |
| T = 12 Subjected to natural light | | |
| 9% | 6.8% | 15.8% |

4.—Conclusion

*Hypericum perforatum* L oleoresins obtained according to the invention are stable and the hyperforin content is not decreased with either temperature or light.

EXAMPLE 3
Illustrating the Regulation of the Production of the Components of the Extracellular Membrane.

Cellular Cultures

The fibroblasts were obtained from surgical material. The skin samples were pre-incubated for 2 hours at 40° C. in RPMI 1640 with 2% penicillin/streptomycin. The fatty tissues were eliminated and the skin was cut into small pieces and fixed to culture dishes dampened with foetal calf serum (FCS). The pieces of skin were incubated at 37° C. in a $CO_2$ atmosphere in RPMI with 10% FCS and 1% penicillin/streptomycin. The culture medium was changed twice a week. The fibroblast culture was trypsinised (trypsin/EDTA: 0.0%/0.02%) and a subculture was started, using the cells from the $4^{th}$ to the 14th Collagen Synthesis The human fibroblasts were grown in microplates for cell tissues. Each plate was inoculated with 10,000 cells in 100 μl of RMPI medium supplemented with FCS (10%) and ascorbic acid (50 μl/ml). After 24 hours of incubation in a humid $CO_2$ atmosphere at 5%, the culture medium was changed for 100 μl of fresh medium per plate containing different concentrations of the extract to be analysed and 1μ Ci $^3$H of marked proline. After 24 hours of incubation, the collagen was extracted from each plate by adding 100 μl of 1M acetic acid that contained 1 mg/ml of pepsin and stored at 4° C. throughout the night. The content of the plates was transferred to polypropylene tubes to which 800 μl of 0.5M acetic acid containing a neutral soluble rat skin collagen salt (200 μl) as a dilutant, was added. The tubes were centrifuged at 4000 g for 20 minutes. The collagen was precipitated from the supernatant by adding 250 μl of NaCl in acetic acid (25%) per tube. After 2 hours, the tubes were centrifuged at 4000 g for 30 minutes, the precipitates were re-dissolved in 300 μl 0.15 M NaCl in 0.05 M tris-HCl, pH 7.5. The collagen was precipitated by adding 2 ml of 4.5 M NaCl in the same buffer. After 2 hours, the tubes were centrifuged at 4000 g for 30 minutes. The supernatant was discarded and the collagen precipitates were washed in 2 ml of 2% ethanol and centrifuged at 4000 g for 30 minutes. Finally, each precipitate was dissolved in 250 μl of acetic acid 0.5 M, taken to a scintillation vial and measured in a liquid scintillation counter with an external standard.

The percentage of incorporation of collagen for different concentrations of oleoresin are showed as follows. The value indicated is the average from 4 parallel experiments.

% of incorporation of $H^3$-proline in the collagen.

| CONTROL | 100% |
|---|---|
| 0.1% Ethanol | 126% |
| 0.01 μg/ml | 120% |
| 0.1 μg/ml | 115% |
| 0.5 μg/ml | 130% |
| 1 μg/ml | 170% |
| 5 μg/ml | 20% |
| 10 μg/ml | 10% |
| 50 μg/ml | 20% |

Tenascine

The fibroblasts were grown on microplates with a density of 20,000 cells per plate in RPMI medium without FCS. After 24 hours at 37° C. in a 5% $CO_2$ atmosphere, the culture medium was changed. The cells were incubated for 48 hours more at 37° C. with different concentrations of oleoresin. The cells were washed three times with PBS with 1% BSA and 0.1% Tween 20. The cells were fixed with a methanol/acetone solution (1:1), washed 3 times as described above, and incubated with a monoclonal anti-tenascine antibody for 1 hour at 37° C. After washing, the cells were incubated with a monoclonal anti-mouse goat antibody with alkaline phosphatase. The cells were washed 3 times and incubated with p-nitrophenyl phosphate (1 mg/ml) for 15 minutes. The microplates were centrifuged at 200 g and 100 μl of the supernatant were transferred to a new microplate. The plates were read in an ELISA reader at 405 nm.

The percentage of the tenascine content compared to the control for different concentrations of oleoresins is shown as follows, where the values are the average from 3 experiments.

% de tenascine compared to the control.

| CONTROL | 100% |
|---|---|
| 0.1% Ethanol | 115% |
| 0.1 μg/ml | 90% |
| 0.5 μg/ml | 60% |
| 1 μg/ml | 50% |
| 5 μg/ml | 40% |
| 10 μg/ml | 30% |
| 20 μg/ml | 20% |

EXAMPLE 4

Illustrating the Results Obtained by the Hydrosoluble *Hypericum perforatum* L Oleoresin Gel in the Cicatrizant Product A Hydrosoluble gel with a content of 0.1% of *Hypericum perforatum* L oleoresin.

Product B

Hydrosoluble gel with a content of 0.5% of *Hypericum perforatum* L oleoresin.

Group 1

12 patients with dermatological pathology requiring removal by electric scalpel, liquid nitrogen or laser, with no need for sutures. The burns are treated clinically.

Group 2

Patients with dermatological disease requiring removal and surgical closure with sutures. Wounds treated clinically.

| Group 1 results 1: Surgical burns. | | | | |
|---|---|---|---|---|
| | Pain | Erythema | Infection | Crust |
| | | 48-hour control. | | |
| Product A | Slight | Slight | No | Yes |
| Product B | Moderate | Slight | Slight | Yes |
| | | 7-day control. | | |
| Product A | No | No | No | HGT |
| Product B | No | No | No | GNT |

GNT: Normal granulation tissue.
HGT: Haemorrhagic granulation tissue.

15-Day Control.

In both groups, no hypertrophic of cheloid scars were observed.

| Group 2 results: surgical wounds. | | | | | |
|---|---|---|---|---|---|
| | Pain | Erythema | Infection | Crust | Suture |
| | | 48-hour control. | | | |
| Product A | Moderate | Moderate | Slight | Initial | Normal |
| Product B | Moderate | Moderate | Moderate | No | Normal |
| | | 7-day control | | | |
| Product A | No | No | No | Yes | Removed |
| Product B | No | No | No | Yes | Removed |

15-Day Control.

No hypertrophic or cheloid scars were observed.

Conclusions

Cicatrizant effect

The products have been well tolerated and neither inflammation or infection has appeared.

There is no hypertrophic scarring

The lesions are easily monitored without removing the product.

No maceration of the skin was observed.

What is claimed is:

1. A. *Hypericum perforatum* L oleoresin comprising not less than 10% by weight of total hyperforins and not less than 0.5% by weith of hypercins, wherein said oleoresin does not contain preservatives, and the content of said total hyperforins in said oleoresin does not substantially decrease over time, wherein said oleoresin is obtained by the process comprising the steps of: less than 10% of hyperforin and no less than 0.5% of (A) extracting *Hypericum perforatum* L with at least one organic solvent having a polarity of less than 0.6 to obtain an extract;

(B) evaporating the solvent from the resulting extract of step (A) to obtain a product;

(C) dissolving the resulting product of step (B) with an alcohol-water mixture at 40–50° C. to obtain a solution;

(D) filtering the resulting solution of step (C) to obtain a filtrate; and (E) subjecting the resulting filtrate of step (D) to evaporation at low pressure.

2. A composition for regulating the production of components of the extracellular matrix in human fibroblasts comprising the *Hypericum perforatum* L oleoresin of claim 1, and a pharmaceutically acceptable diluent.

3. A composition for regulating the production of components of the extracellular matrix in human fibroblasts comprising the *Hypericum perforatum* L oleoresin of claim 1, and a pharmaceutically acceptable diluent.

4. The composition of claim 3, wherein said components comprise collagen.

5. The composition of claim 3, wherein said components comprise tenascine.

6. A hydrosoluble gel useful as a cicatrizant, comprising, as an active ingredient, the *Hypericum perforatum* L oleoresin of claim 1, and a diluent, a gelling agent, a humidifying agent, an emulsifier and a preservative.

7. The hydrosoluble gel of claim 6, wherein said diluent is water.

8. The hydrosoluble gel of claim 6, wherein said gelling agent is glyceryl polyacrylate.

9. The hydrosoluble gel of claim 6, wherein said humidifying agent is glycerine.

10. The hydrosoluble gel of claim 6, wherein said emulsifying agent is selected from the group consisting of PEG40-hydrogenated castor oil, polysorbate-20, octoxinole-11 and mixtures thereof.

11. The hydrosoluble gel of claim 6, wherein said preservative is a parabene.

12. A process for obtaining a hydrosoluble gel comprising the steps of:

(A) dissolving the *Hypericum perforatum* L oleoresin of claim 1 in an emulsifier to obtain a first solution;

(B) dissolving a preservative in water to obtain a second solution;

(C) admixing the resulting first solution of step (A) with the resulting second solution of step (B) to obtain a third solution; and (D) admixing a humidifying agent and a gelling agent with the resulting third solution of step (C) to obtain said gel.

13. A process for obtaining a *Hypericum perforatum* L oleoresin having a stable content of total hyperforins comprising the steps of:

(A) extracting *Hypericum perforatum* L with at least one organic solvent having a polarity of less than 0.6 to obtain an extract;

(B) evaporating the solvent from the resulting extract of step (A) to obtain a product;

(C) dissolving the resulting product of step (B) with an alcohol-water mixture at 40–50° C. to obtain a solution;

(D) filtering the resulting solution of step (C) to obtain a filtrate; and (E) subjecting the resulting filtrate of step (D) to evaporation at low pressure.

14. The process of claim 13, wherein said alcohol is selected from the group consisting of methanol, ethanol and isopropanol.

15. The process of claim 13, wherein said alcohol-water mixture is ethanol:water (60:40).

16. The process of claim 13, wherein said *Hypericum perforatum* L is *Hypericum perforatum* L which has been dried at less than 35° C.

17. The process of claim 13, wherein the content of total hyperforins in said *Hypericum perforatum* L is over 2% by weight.

* * * * *